United States Patent [19]

Larock et al.

[11] Patent Number: 5,233,059

[45] Date of Patent: Aug. 3, 1993

[54] SYNTHESIS OF BENZOPROSTACYCLINS USING PALLADIUM CATALYSIS

[75] Inventors: Richard C. Larock, Ames, Iowa; Nam H. Lee, Urbana, Ill.

[73] Assignee: Iowa State University Research Foundation, Inc., Ames, Iowa

[21] Appl. No.: 735,428

[22] Filed: Jul. 25, 1991

[51] Int. Cl.$^5$ ............................................. C07D 307/93
[52] U.S. Cl. ..................................................... 549/458
[58] Field of Search ......................................... 549/458

[56] References Cited

U.S. PATENT DOCUMENTS

| | | | |
|---|---|---|---|
| 4,206,127 | 6/1980 | Woessner | 260/345.2 |
| 4,230,879 | 10/1980 | Wissner | 560/121 |
| 4,301,164 | 11/1981 | Ohno et al. | 424/263 |
| 4,335,054 | 6/1982 | Balser et al. | 260/465 D |
| 4,402,824 | 8/1983 | Aristoff | 549/385 |
| 4,474,802 | 10/1984 | Ohno et al. | 549/458 |
| 4,543,421 | 9/1985 | Corey et al. | 560/106 |
| 4,668,814 | 5/1987 | Aristoff | 560/51 |
| 4,683,330 | 7/1987 | Aristoff | 560/51 |
| 4,873,360 | 10/1989 | Johnson et al. | 560/121 |
| 4,902,811 | 2/1990 | Mori et al. | 549/359 |
| 5,004,739 | 4/1991 | DiNinno et al. | 519/220 |

FOREIGN PATENT DOCUMENTS 0274064  7/1988  European Pat. Off. .

OTHER PUBLICATIONS

*Aldrichimica Acta,* "New Listings", Aldrich Chemical Company, Inc., Milwaukee, WI (Publisher), vol. 16, at page 14 (1983).
G. Born, "Aggregation of Blood Platelets by Adenosine Diphosphate and Its Reversal", *Nature,* 194:927 (1962).
D. Deardorff et al., "A Palladium-Catalyzed Route to Mono-and Diprotected Cis-2-Cyclopentene-1,4-Diols", *Tetrahedron Letters,* 26:5615 (1985).
G. Keck et al., "-Stannyl Enones as Radical Traps: A Very Direct Route to PGF$_{2\alpha}$", *J. Org. Chem.,* 52:2958 (1987).
R. Johnson et al., "The Chemical Structure of Prostaglandin X (Prostacyclin)", *Prostaglandins,* 12:915 (1976).
S. Moncada et al., "An Enzyme Isolated from Arteries Transforms Prostaglandin Endoperoxides to an Unstable Substance that Inhibits Platelet Aggregation", *Nature,* 263:663 (1976).
H. Nagase et al., "Synthesis of (+)-5,6,7-Trinor-4,-8-Inter-M-Phenylene PGI$_2$", *Tetrahedron Letters,* 31:4493 (1990).
R. Noyori et al., "Synthetic Applications of the Enantioselective Reduction by Binaphthol-Modified Lithium Aluminum Hydride Reagents", *J. Am. Chem. Soc.,* 106:6717 (1984).
M. Ochiai et al., "A New Synthesis of T-Hydroxyvinylstannanes and Silanes Utilizing β-Stannylvinyl and β-Silylvinyl Sulfones", *Tetrahedron Letters,* 24:4025 (1983).
J. Stille, "The Palladium-Catalyzed Cross-Coupling Reactions of Organotin Reagents with Organic Electrophiles", *Angew. Chem. Int. Ed. Engl.,* 25:508 (1986).

*Primary Examiner*—James H. Reamer
*Attorney, Agent, or Firm*—Merchant, Gould, Smith, Edell, Welter & Schmidt

[57] ABSTRACT

A method is provided for preparing benzoprostacyclins by the palladium-catalyzed tandem alkene insertion into a 1,4-bisoxy-substituted cyclopent-2-ene intermediate.

15 Claims, No Drawings

SYNTHESIS OF BENZOPROSTACYCLINS USING PALLADIUM CATALYSIS

BACKGROUND OF THE INVENTION

Prostacyclin (I, PGI$_2$), first discovered in 1976, is one of the most potent natural inhibitors of blood platelet aggregation. (See S. Moncado et al., Nature, 263, 663 (1976) and R. Johnson et al., Prostaglandins, 12, 915 (1976)). Unfortunately, its low metabolic stability due to enol ether hydrolysis greatly diminished its pharmacological utility. Major interest of late has focused on the synthesis of more stable analogs, such as the benzoprostacyclins Ia-c, described by K. Ohno et al. in U.S. Pat. No. 4,301,164.

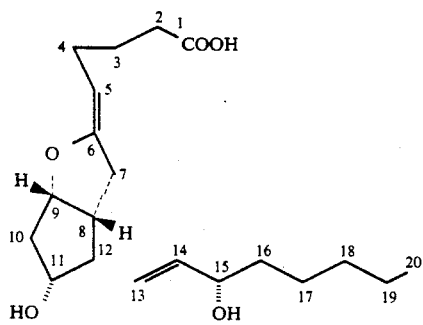

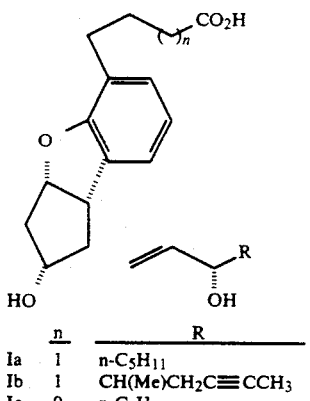

| | n | R |
|---|---|---|
| Ia | 1 | n-C$_5$H$_{11}$ |
| Ib | 1 | CH(Me)CH$_2$C≡CCH$_3$ |
| Ic | 0 | n-C$_5$H$_{11}$ |

These compounds similarly exhibit substantial inhibition of platelet aggregation.

Present synthetic approaches to the benzoprostacyclins are very lengthy and rather inefficient. For example, the synthesis of compound Ia as reported by H. Nagase et al., Tetrahedron Lett., 31, 4493 (1990) requires 23 steps. As reported by K. Ohno et al. in U.S. Pat. No. 4,474,802, the synthesis of the C$_1$-methyl ester of Ib requires at least 17 steps.

Therefore, a need exists for efficient methods to synthesize benzoprostacyclins.

SUMMARY OF THE INVENTION

The present invention provides a method for the synthesis of benzoprostacyclins of general formula II.

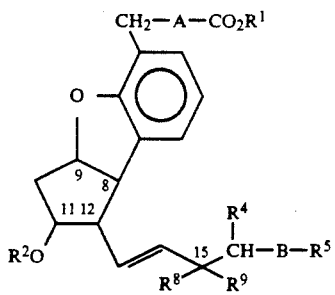

wherein R$^1$ is a pharmaceutically acceptable cation, H or (C$_1$-C$_{12}$)alkyl, preferably (C$_1$-C$_4$)alkyl; R$^2$ is H, (C$_1$-C$_{12}$)-alkyl, (C$_2$-C$_{10}$)acyl or (C$_7$-C$_{13}$)aroyl; R$^8$ is H or (C$_1$-C$_{12}$)alkyl, and R$^9$ is OR$^3$ wherein R$^3$ is H, (C$_1$-C$_{12}$)alkyl, (C$_2$-C$_{10}$)acyl, or (C$_7$-C$_{13}$)aroyl; or R$^8$ and R$^9$ taken together are keto; R$^4$ is H, F, methyl or ethyl; R$^5$ is (C$_1$-C$_5$)alkyl; A is —CH$_2$—, —O—CH$_2$—, —CH$_2$—CH$_2$— or —CH=CH—, and B is —(CH$_2$)$_n$—Z— wherein n is 0-4 and Z is —CH$_2$—CH$_2$—, —CH=CH— or —C≡C—.

In compound II, the bonds at cyclopentane ring positions 8, 9 11 and 12, individually are in either the alpha (extending below the plane of the cyclopentane ring, indicated by a broken line) or beta (extending above the plane of the cyclopentane ring, indicated by a wedged line) configuration, with the "natural" configuration shown for 1. The all-alpha or all-beta configurations are readily prepared by the present method. The configuration at C$_{15}$ may be either (R) or (S). Preferably, the C$_8$ and C$_9$ cyclopentane ring bonds are both alpha (the "natural" configuration) or both beta.

Two novel compounds which can be prepared in accord with the present method wherein R$^1$, A, R$^2$, R$^3$, R$^4$, B and R$^5$ are as described hereinabove, are depicted below (IIa, IIb).

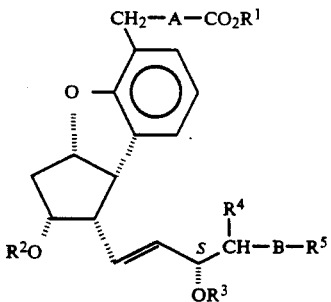

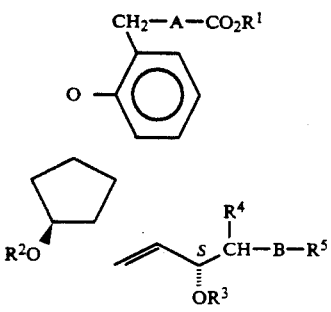

Representative compounds of formula II, wherein A=—CH$_2$—CH$_2$—, R$^2$=R$^3$=R$^4$=H, B=—(CH$_2$)$_3$— and $R^5=CH_3$, which were prepared in accord with the present method are listed in Table I, below.

TABLE I

Benzoprostacyclin Analogs

| Compound No. | Bond Orientation | | | | |
|---|---|---|---|---|---|
| | $C_8$ | $C_9$ | $C_{12}$ | $C_{13}$ | $C_{15}$—OH |
| 16 ($R^1$ = Et) | α | α | α | α | $C_{15}$ =O |
| 17 ($R^1$ = Et) | α | α | α | α | α |
| 18 ($R^1$ = Et) | α | α | α | α | β |
| 17 ($R^1$ = H) | α | α | α | α | α |
| 18 ($R^1$ = H) | α | α | α | α | β |
| 19 ($R^1$ = Et) | β | β | β | β | α |

The present invention is also directed to intermediate III, which is employed in the present synthetic method:

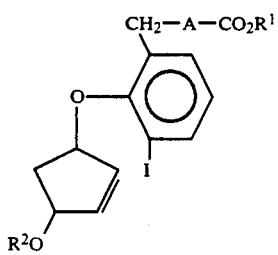

(III)

wherein $R^1$ is ($C_1$-$C_{12}$) alkyl and A and $R^2$ are as defined above. Preferably, the 1,4-cyclopentenyloxy bonds are both alpha, $R^2$ is H, and $R^1$ is ($C_1$-$C_4$)alkyl.

As used herein, the term "alkyl" includes branched or straight-chain alkyl groups, or ($C_3$-$C_{12}$)cycloalkyl, preferably ($C_3$-$C_6$)cycloalkyl. Aroyl is preferably benzoyl or naphthoyl, wherein the aryl ring is either unsubstituted or is substituted with 1-4 ($C_1$-$C_4$)alkyl or 1-4 ($C_1$-$C_4$)alkoxy groups. The preferred acyl is acetyl. Preferably A and B are methylene (—$CH_2$—) or ethylene (—$CH_2$—$CH_2$—). Preferred pharmaceutically-acceptable cations are alkali metal salts, $NH_4^+$, or the carboxylic acid addition salts of non-toxic amines.

In accord with the present method, a compound of the formula III, wherein $R^2$ is as defined above, and preferably is H; $R^1$ is as defined above, and preferably is ($C_1$-$C_{12}$)alkyl and A is as defined above, and preferably is —$CH_2$— or —$CH_2$—$CH_2$—, is reacted with a compound of the formula IV:

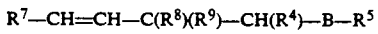

$R^7$—CH=CH—C($R^8$)($R^9$)—CH($R^4$)—B—$R^5$    IV wherein $R^7$ is H, tris($C_1$-$C_4$)alkylSn or (phenyl)$_3$Sn; $R^8$ is H or ($C_1$-$C_{12}$)alkyl and $R^9$ is $OR^3$; or $R^8$ and $R^9$ taken together are keto; and $R^3$, $R^4$, B and $R^5$ are as described hereinabove; in the presence of a catalytic amount of palladium(O)(Pd(O)), and an organic base to directly yield the corresponding compound of formula II. When $R^7$ is trialkylSn- or triphenylSn, preferably $R^8$ is H and $R^9$ is OH. Preferably, the reaction is carried out in the presence of an organic amine, preferably i-Pr$_2$NEt, most preferably also in the presence of a source of chloride ion (Cl⁻), such as an alkali metal chloride or a tetraalkylammonium chloride, such as n-Bu$_4$NCl.

When $R^8$ and $R^9$ together are keto, the keto group can then be reduced to the corresponding $C_{15}$-hydroxy group by methods known to the art. Optionally, in either case, the $C_1$-ester can then be saponified if necessary, to yield compounds of formula II wherein $R^1$ is H, and the $CO_2H$ group can also be converted into a pharmaceutically-acceptable carboxylate salt.

The moiety —CH=CH— may be cis or trans. It is preferably trans in compound IV, and cis in moieties A and B in compounds II or III.

DETAILED DESCRIPTION OF THE INVENTION

The preparation of a preferred embodiment of intermediate III is summarized in Scheme 1.

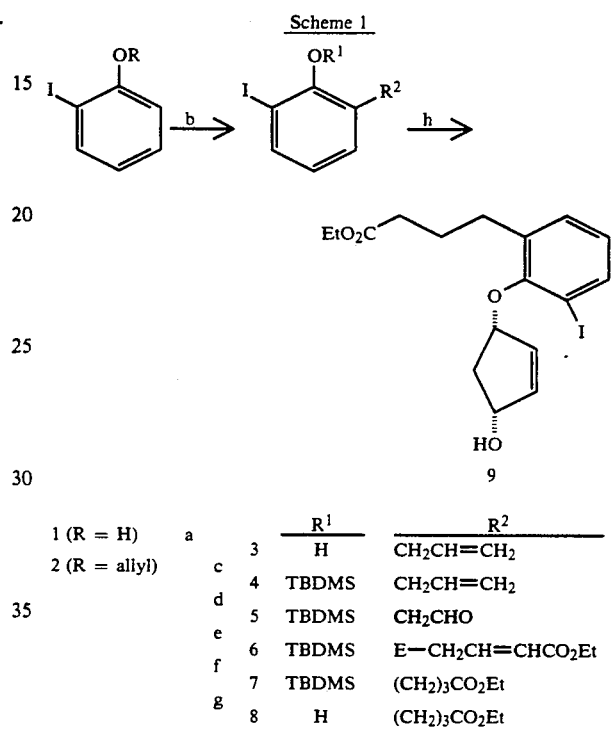

Scheme 1

| | | | $R^1$ | $R^2$ |
|---|---|---|---|---|
| 1 (R = H) | a | 3 | H | $CH_2CH=CH_2$ |
| 2 (R = allyl) | c | 4 | TBDMS | $CH_2CH=CH_2$ |
| | d | 5 | TBDMS | $CH_2CHO$ |
| | e | 6 | TBDMS | E—$CH_2CH=CHCO_2Et$ |
| | f | 7 | TBDMS | $(CH_2)_3CO_2Et$ |
| | g | 8 | H | $(CH_2)_3CO_2Et$ |

Steps (a)–(g) are summarized in Table II below, wherein the numbers preceding the reactants are mole ratios: 1 mole of 1-8, unless otherwise noted.

TABLE II

Synthesis of Compound 9

| Step | Reactants | Yield |
|---|---|---|
| a | 1.2 allyl bromide, 1.2 $K_2CO_3$, acetone | 94% |
| b | 0.8 MeAlCl$_2$, −20° C. | 70% |
| c | t-butyldimethylsilyl chloride, imidazole | 90% |
| d | ozone, −78° C./Me$_2$S | 83% |
| e | Ph$_3$P=CHCO$_2$Et | 83% |
| f | H$_2$, cat. PtO$_2$ | 90% |
| g | n-Bu$_4$NF | 94% |
| h | 1,5-cyclopentadiene monoepoxide, 2% Pd(PPh$_3$)$_4$, THF | 72% |

The requisite regio- and stereochemistry is efficiently introduced by the palladium-catalyzed opening of a vinylic epoxide. See, D. R. Deardorff et al., *Tetrahedron Lett.*, 26, 5615 (1984).

The reaction of 9 with 1-octen-3-one, n-Bu$_4$NCl and i-Pr$_2$NEt, in a mole ratio to 9 of 10:1.1:2.5, respectively, proceeded in 43% yield in the presence of 5% Pd(OAc)$_2$ at 50° C. in DMF to give compound 16, as shown in Scheme 2, below.

Scheme 2

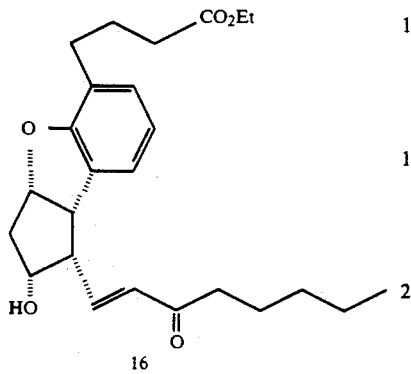

Mechanistically, this process is believed to involve (1) reduction of Pd(OAc)$_2$ to Pd(O), (2) oxidative addition of the aryl iodide of 9 to Pd(O) (without apparent competitive displacement of the aryloxy group to form a π-allylpalladium intermediate which would deactivate the catalyst), (3) intermolecular syn insertion of the cyclopentene double bond to form a bicyclic alkylpalladium intermediate which is blocked from syn palladium β-hydride elimination by the hydroxy group, (4) enone insertion into the carbon-palladium bond, and finally (5) palladium β-hydride elimination to the enone 16 (subsequent palladium hydride decomposition of Pd(O) regenerates the catalyst and completes the catalytic cycle).

(S)-BINAL-H reduction of enone 16 in accord with the procedure of R. Noyori et al., *J. Amer. Chem, Soc.*, 106, 6717 (1984), was unselective, affording an easily separable 1:1 mixture of diastereomers in 50% yield, in accord with Scheme 3, below.

Scheme 3

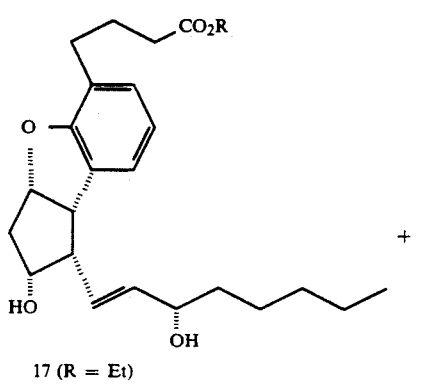

-continued
Scheme 3

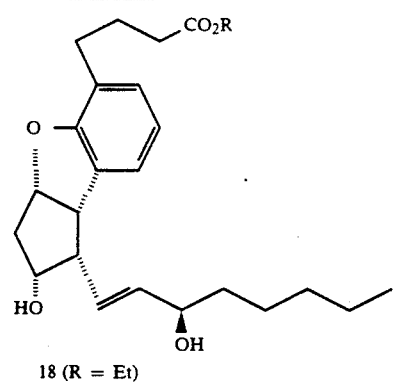

Saponification of esters 17 (R=Et) and 18 (R=et) afforded the corresponding carboxylic acids 17 (R=H) and 18 (R=H) in 83% and 92% yields, respectively.

These stereochemical difficulties can be overcome in part by replacing the 1-alken-3-one in Scheme 2 with chiral vinylic stannane 14 as shown in Scheme 4. A separable mixture of diastereomers 17 (R=Et) and 19 (R=Et) was obtained in 30% overall yield.

Scheme 4

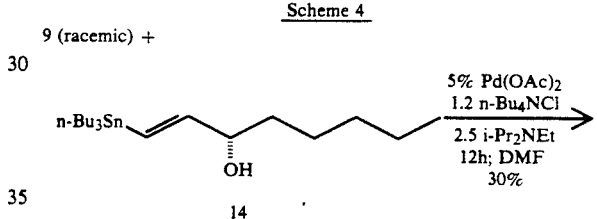

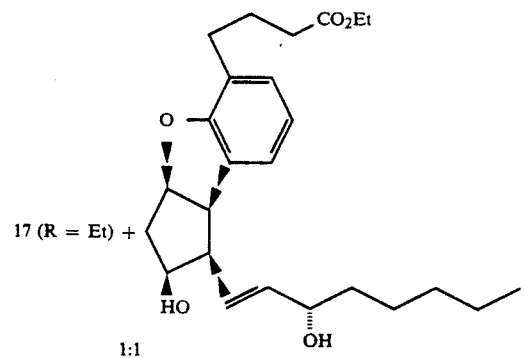

SYNTHETIC METHODOLOGY

The compound which is the source of the Pd(O) catalyst is generally employed in an amount of about 0.001-20 mol-%, preferably 0.1-10 mol-%, based on the compound of formula III. Useful catalysts include, for example, bis(dibenzylideneacetone)palladium (O), bis-(isonitrile)palladium (O), bis-(cyclohexylisonitrile)palladium(O), bis-(isopropylisonitrile)palladium(O), bis-(tert.-butylisonitrile)-palladium(O), bis-(p-tolylsionitrile)palladium(O), bis-(phenylisonitrile)palladium (O), and bis-(p-methoxyphenylisonitrile)palladium (O).

Other Pd-containing compounds, e.g., Pd(II) compounds, can also be used in the present method under conditions wherein Pd(O) is generated. These include PdCl$_2$, palladium(II) carboxylate salts, such as Pd(OAc)$_2$, PdBr$_2$, Pd(CN)$_2$, Pd(NO$_3$)$_2$ and the like.

Other Pd catalysts which can be used in the present method include those disclosed in Blaser et al. (U.S. Pat. No. 4,335,054) at Col. 6, line 5 to Col. 7, line 3.

Bases used in the present process can be inorganic or organic bases, which are adequately soluble in the reaction medium. Representative bases are disclosed at Col. 7, lines 8-65 of the Blaser et al. patent. Inorganic bases for use in the present process include $Na_2CO_3$, $KHCO_3$, $Li_2CO_3$, and $NaHCO_3$. Useful organic bases include trialkylamines, such as diisopropyl(ethyl)amine. Preferably, organic bases are used. The preferred mole ratio of the base to the compound of formula III is about 2-3:1.

A source of halide, such as chloride ion, is also preferably used in the present process, in an amount effective to promote the reaction and increase the yield. Organic chloride sources such as tetra(alkyl)ammonium chlorides, wherein the alkyls can each be about $(C_2-C_{12})$-alkyl, are preferred, i.e., $(n-Bu)_4NCl$. Alkali metal halides such as MX, wherein M is Li, Na, or K and X is Cl, Br or I, can also be used. Preferred in the present method are a mixture of diisopropyl(ethyl)amine and tetra-n-butylammonium chloride (n-Bu$_4$NCl). The halide source is preferably used in only a slight excess over the compound of formula III, (1.1-1.5 equivalents).

In carrying out the synthesis of the compound of formula II, the aryl iodide III is preferably combined with an excess of compound IV, e.g., preferable in a mole ratio of III:IV of about 1:1.25-20, in a suitable organic solvent. The reaction mixture is preferably stirred at about 20°-75° C. for about 5-48 hr. under an inert atmosphere. The crude product is extracted, i.e., into ethyl acetate and can be purified by chromatography.

Useful organic solvents include tetrahydrofuran (THF), ethers, glycol ethers, dimethylsulfoxide, dimethylformamide (DMF), acetonitrile, acetamide, dimethylacetamide, and hexamethylphosphoramide.

Compounds of formula IV, wherein $R^7=H$ and $R^8$ and $R^9$ taken together are keto, e.g., vinyl(alkyl or alkylene)ketones can be readily prepared, e.g., by the reaction of vinylmagnesium bromide with acid chlorides of the general formula $R^5-B-(R^4)CH-COCl$, wherein $R^5$, B and $R^4$ are as described above. Compounds of formula IV, wherein $R^7$ is a trialkylstannyl group, $R^8$ is H and $R^9$ is $OR^3$ can be prepared as disclosed by J. K. Stille in *Angew. Chem. Int. Ed. Engl.*, 25, 508 (1986), M. Ochiai et al., *Tet. Letters*, 24, 4025 (1983), and by G. Keck et al., *J. Org. Chem.*, 52, 2958 (1987). For example tri-n-butyltin hydride can be reacted with a protected 3-hydroxy-1-alkyne as disclosed in U.S. Pat. No. 4,230,879.

The reduction of $C_{15}$-keto-benzoprostacyclins to yield compounds of formula II, wherein $R^3=H$ can be accomplished with borohydride reducing agents such as zinc borohydride or sodium borohydride, or with chiral reducing agents such as lithium aluminum hydride/α, α'-binaphthol ((S)-BINAL-H), as described in detail in the working Examples, below and in *Aldrichimica Acta*, 6, 14 (1983). The free $C_{11}$—OH or $C_{15}$—OH groups can then be acylated or aroylated by conventional methodologies, e.g., via reaction with anhydrides or acid chlorides in the presence of an organic base. Compounds of formula II wherein $R^1$ is alkyl can be converted into the corresponding carboxylic acids by saponification with alkali metal hydroxides in alcoholic solvents followed by neutralization of the reaction mixture. Pharmaceutically-acceptable cations ($R^1$) include alkali metal salts and the amine salts disclosed in K. Ohno et al. (U.S. Pat. No. 4,474,802), which is incorporated by reference herein.

The reaction methodology employed to prepare compound 9, as outlined in Scheme 1, can be readily modified to prepare other aryl iodides of general formula III, e.g., by the use of aldehydes of varying chain length in step (e). Compound III wherein A is CH=CH and $R^2$ is H is readily prepared by deprotecting compound 6, e.g., via step (g).

BIOASSAYS

The compounds prepared by the present method exhibit potent platelet aggregation inhibiting activity and blood pressure decreasing activity by vasodilation. The efficacy of the compound to inhibit platelet aggregation is examined according to Born's method (*Nature*, 194, 927 (1962)). The blood is collected from humans or anesthetized rabbits. The blood is anti-coagulated with a 3.8% aqueous solution of sodium citrate in an amount of a tenth volume of the blood and centrifuged for 10 minutes at 200×g to obtain platelet rich plasma. After pretreatment of the platelet rich plasma with the benzoprostacyclin, aggregation is measured by aggregometer with arachidonic acid, adenosine-2-phosphate(ADP) or collagen as the aggregation inducer. It is shown that compounds 16 (R=Et), 17 (R=Et), 18 (R=Et), 17 (R=H), 18 (R=H), and 19 (R=Et) exhibit potent inhibitory activity.

To examine the efficacy of a benzoprostacyclin to reduce blood pressure, the blood pressure of the carotid artery of rats under pentobarbital anesthesia is measured. The compounds listed above are injected into the vein through an indwelling catheter. These compounds exhibit substantially the same activity as prostaglandin $E_1$ at the same dose of 0.05 to 100 μg/kg and have a longer duration of action than prostaglandin $E_1$.

An anti-thrombotic agent containing any of these benzoprostacyclins as the active component may be applied to prevent clotting in extracorporeal circulation, treatment of a disturbance of peripheral circulation such as Buerger's disease and Raynaud's disease, prevention and treatment of myocardial infarction, angina pectoris and cerebral infarction, prevention of TIA, treatment of diabetic thrombosis and prevention and treatment of arteriosclerosis.

For the treatment of Buerger's disease, the pharmacologically effective intravenous dose of a compound of the invention is 0.001 to 100 μg/kg/min. In case of using the compound as an anti-thrombotic agent, 0.001 to 50 mg of the compound is orally administered to a patient one to three times a day, and in case of using the compound as a blood pressure-reducing agent, 0.01 to 50 mg of the compound is orally administered to a patient one to three times a day.

The benzoprostacyclins can be orally administered as a form of a solid substance containing excipients such as starch, lactose, and sucrose, or can be parenterally administered in a form of a sterilized aqueous solution. Such a solution may contain another solute, for instance, glucose or sodium chloride in an amount sufficient to make the solution isotonic. Various preparations for oral administration, injections, infusions, eye drops and suppositories can be prepared.

The invention will be further described by reference to the following detailed examples.

EXAMPLE 1

Preparation of Compound 2

A solution of o-iodophenol (6.6 g, 30 mmol), allyl bromide (4.0 g, 33 mmol) and potassium carbonate (4.6 g, 3.3 mmol) in 7.5 ml of acetone was refluxed for 8 hr. The reaction mixture was diluted with 40 ml of water, and extracted with ether (2×25 ml). The organic phase was washed with brine (25 ml), and then dried over $MgSO_4$. Concentration, followed by flash chromatography, gave compound 2 as a colorless oil: 6.8 g, 94% yield; $^1H$ NMR ($CDCl_3$) δ 7.77 (dd, J=17.4 and 10.5 and 7.8 Hz, 1.5 Hz, 1 H, Ar), 7.27 (dt, J=1.8 and 7.8 Hz, 1 H, Ar), 6.80 (dd, J=7.8 and 1.2 Hz, 1 H, Ar), 6.70 (dt, J=7.8 and 1.2 Hz, 1 H, Ar), 6.06 (ddt, J=17.4 and 10.5 and 7.8 Hz, 1 H, HC=C), 5.52 (dd, J=17.4 and 1.8 Hz, 1 H, HC=C), 5.31 (dd, J=10.5 and 1.2 Hz, 1 H, HC=C), 4.59 (dt, J=4.8 and 1.5 Hz, 2 H, $CH_2$); $^{13}C$ NMR ($CDCl_3$) δ 157.09, 139.51, 132.57, 129.35, 122.66, 117.59, 112.58, 86.72, 69.68; IR (neat) 1582, 1477 $cm^{-1}$.

EXAMPLE 2

Preparation of 6-allyl-2-iodophenol 3

To a solution of compound 2 (7.0 g, 27 mmol) in 130 ml of hexane was added $MeAlCl_2$ (Aldrich, 1.0 M in hexane, 22 ml 22 mmol) dropwise at −20° C. After the reaction mixture was stirred for 2 hr. at −20° C. under nitrogen, the reaction was quenched by adding water (40 ml) and the mixture slowly warmed to room temperature with swirling. Ethyl acetate (30 ml) was added to the reaction mixture, then stirring was continued for 5 min. After separating phases, the organic phase was washed with water (30 ml) and brine (30 ml), then dried and concentrated. The residue was purified by flash chromatography with 15:1 hexane/EtOAc to give product 3: 4.9 g, 70% yield; $R_f$=0.38 (20:1 hexane/EtOAc); $^1H$ NMR ($CDCl_3$) δ 7.51 (dd, J=1.2 and 7.8 Hz, 1 H, Ar), 7.07 (d, J=7.8 Hz, 1 H, Ar), 6.62 (t, J=7.8 Hz, 1 H, Ar), 5.98 (ddt, J=17.4 and 9.6 and 6.6 Hz, 1 H, HC=C), 5.37 (s, 1 H, OH), 5.12 (m, 1 H, CH=C), 5.07 (m, 1 H, CH=C), 3.43 (d, J=6.6 Hz, 2 H, $CH_2$); $^{13}C$ NMR ($CDCl_3$) δ 152.60, 136.33, 136.01, 130.73, 126.81, 122.42, 116.22, 86.41, 35.56; IR (neat) 3487 (OH), 1593, 1234 $cm^{-1}$; LRMS m/z (relative intensity) 51.1 (34), 77.1 (47), 105.1 (58), 118.1 (41), 133.1 (42), 260.0 ($M^+$, 100).

EXAMPLE 3

Preparation of Compound 4

To a solution of compound 3 (4.9 g, 18.7 mmol) and imidazole (3.2 g, 47.1 mmol) in 20 ml of DMF was added t-butyldimethylsilyl chloride (3.1 g, 20.5 mmol) dissolved in 15 mmol of DMF at room temperature under nitrogen. After the mixture was stirred for 12 hr. at room temperature, it was extracted with hexane (50 ml×8). The hexane phase was concentrated and then flash chromatographed to give compound 4: 6.3 g, 90% yield; $R_f$=0.52 (hexane); $^1H$ NMR ($CDCl_3$) δ 7.63 (dd, J=7.8 and 1.8 Hz, 1 H, Ar), 7.11 (dd J=7.8 and 1.8 HZ, 1 H, Ar), 6.66 (t, J = 7.8 Hz, 1 H, Ar), 5.86 (ddt, J=17.4 and 9.6 and 6.6 Hz, 1 H, C=$CHCH_2$), 5.08 (m, 2 H, $H_2C$=C), 3.39 (d, J=6.9 Hz, 2 H, $CH_2$), 1.06 (s, 9 H, t-BuSi), 0.331 (s, 6 H, $SiMe_2$).

EXAMPLE 4

Preparation of Compound 5

Ozone was passed through a solution of compound 4 (722 mg, 1.9 mmol) in 19 ml of methanol at −78° C. until the deep blue color persisted (about 15 min.). The reaction was flushed with nitrogen gas and 8 ml of $CH_3SCH_3$ was added at −78° C. The reaction mixture was then allowed to stir for 30 min. at −78° C., for 1 hr. at 0° C and for another 30 min. at room temperature. The methanol solvent was evaporated under reduced pressure, and 60 ml of ether was then added to the residue. After the mixture was washed with water (10 ml) and brine (20 ml×2), it was dried and concentrated. Flash chromatography gave product 5: 638 mg, 83% yield; $R_f$=0.63 (3:1 hexane/EtOAc); $^1H$ NMR ($CDCl_3$) δ 9.63 (t, J=2.1 Hz, 1 H, CHO), 7.74 (dd, J=8.1 and 1.5 Hz, 1 H, Ar), 7.09 (dd, J=7.5 and 1.5 Hz, 1 H, Ar), 6.72 (t, J=7.5 Hz, 1 H, Ar), 3.68 (d, J=2.1 Hz, 2 H, $CH_2$), 1.05 (s, 9 H, t-BuSi), 0.32 (s, 6 H, $SiMe_2$); $^{13}C$ NMR ($CDCl_3$) δ 199.34, 153.92, 139.70, 131.54, 124.26, 123.81, 91.23, 46.16, 26.37, 18.85, −1.52.

EXAMPLE 5

Preparation of Compound 6

To a solution of (carboxymethylene)triphenylphosphorane (Aldrich, 3.88 g, 11.5 mmol) dissolved in 30 ml of $CH_2Cl_2$ was added dropwise at room temperature aldehyde 5 (3.57 g, 9.3 mmol) dissolved in 14 ml of $CH_2Cl_2$. After the reaction was stirred for 12 hr. at room temperature, it was concentrated in vacuo and purified by flash chromatography with 5:1 hexane/EtOAc to give ester 6: 3.52 g, 83% yield; $R_f$=0.46 (5:1 hexane/EtOAc); $^1H$ NMR ($CDCl_3$) δ 7.67 (dd, J=7.8 and 1.5 Hz, 1 H, Ar), 7.05 (dd, J=7.5 and 1.5 Hz, 1 H, Ar), 6.99 (dt, J=15.6 and 6.6 Hz, 1 H, HC=C) 6.66 (t, J=7.5 Hz, 1 H, Ar), 5.80 (d, J=15.6 Hz, 1 H, CH=C), 4.18 (q, J=7.2 Hz, 2 H, $OCH_2$), 3.53 (dd, J=6.9 and 1.5 Hz, 2 H, $CH_2$), 1.27 (t, J=7.2 Hz, 3 H $CH_3$), 1.05 (s, 9 H, t-BuSi), 0.32 (s, 6 H, $Me_2Si$); $^{13}C$ NMR ($CDCl_3$) δ 166.32, 153.31, 146.18, 138.75, 130.60, 129.52, 123.61, 122.93, 91.09, 60.36, 33.94, 26.42, 18.94, 14.32, −1.49.

EXAMPLE 6

Preparation of Compound 7

To a three neck flask equipped with a hydrogen-filled gas balloon were added α,β-unsaturated ester 6 (619 mg, 1.36 mmol), ethanol (20 ml), 2 N aqueous HCl (0.4 ml) and $PtO_2$ (Aldrich, 60 mg). The reaction was flushed with hydrogen gas using an aspirator, and then stirred for 1 hr. at room temperature under the hydrogen balloon pressure. After the reaction was neutralized with 3 N aqueous NaOH (0.27 ml), it was poured into 100 ml of ethyl acetate (EtOAc). The solution was washed with brine (50 ml, 25 ml) and concentrated in vacuo. The residue was purified by flash chromatography to give compound 7: 562 mg, 90% yield; $R_f$=0.52 (7:1 hexane/EtOAc); $^1H$ NMR ($CDCl_3$) δ7.62 (dd, J=7.8 and 1.5 Hz, 1 H, Ar), 7.10 (dd, J=7.8 and 1.5 Hz, 1 H, Ar), 6.64 (t, J=7.8 Hz, 1 H, Ar), 4.11 (q, J=7.2 Hz, 2 H, $OCH_2$), 2.66 (t, J=7.8 Hz, 2 H, $CH_2$), 2.27 (t, J=7.5 Hz, 2 H, $CH_2$), 1.88 (m, 2 H, $CH_2$), 1.25 (t, J=7.2 Hz, 3 H, $CH_3$), 1.04 (s, 9 H, t-BuSi), 0.32 (s, 6 H, $SiMe_2$).

EXAMPLE 7

Preparation of Compound 8

To a solution of compound 7 (2.85 g, 6.2 mmol) in 60 ml of THF at −78° C. was added n-Bu$_4$NF (Aldrich, 1.0 M in THF, 6.2 ml, 6.2 mmol). The reaction mixture was stirred for 1 hr. at −78° C., then allowed to warm to 0° C., and quenched by adding water (10 ml). The mixture was poured into 50 ml of ethyl acetate, and washed with water (25 ml) and brine (20 ml). The organic phase was dried and concentrated. The residue was purified by flash chromatography with 4:1 hexane/EtOAc to give compound 8: 2.02 g, 94% yield; R$_f$=0.37 (5:1 hexane/EtOAc); $^1$H NMR (CDCl$_3$) δ 7.53 (dd, J=7.8 and 1.2 Hz, 1 H, Ar), 7.05 (dd, J=7.8 and 1.2 Hz, 1 H, Ar), 6.58 (t, J=7.8 Hz, 1 H, Ar), 6.18 (s, 1 H, OH), 4.15 (q, J=7.2 Hz, 2 H, CH$_2$), 2.69 (t, J=7.2 Hz, 2 H, CH$_2$), 2.36 (t, J =7.2 Hz, 2 H, CH$_2$), 1.91 (m, 2 H, CH$_2$), 1.27 (t, J=7.2 Hz, 3 H, CH$_3$); $^{13}$C NMR (CDCl$_3$) δ 174.15, 152.96, 136.44, 130.64, 128.05, 122.06, 86.28, 60.59, 33.28, 30.54, 24.68, 14.24; IR (neat) 3373 (OH), 2980, 2957, 1707 (C=O), 1445 cm $^{-1}$. HRMS m/z calculated for C$_{12}$H$_{15}$O$_3$I 334.00660, found 334.00617.

EXAMPLE 8

Preparation of Compound 9

To a dried flask was added Pd(PPh$_3$)$_4$ (18 mg, 0.016 mmol). To this was added compound 8 (264 mg, 0.79 mmol) in 2 ml of THF, and the reaction mixture was stirred in an ice-water bath. Cyclopentadiene monoepoxide (97 mg, 1.18 mmol) in 2 ml of THF was added dropwise at 0° C, and stirring was continued for 20 min. at this temperature and another 24 hr. at room temperature. The reaction mixture was concentrated. The residue was purified by flash chromatography with 2:1 hexane/EtOAc to give product 9: 235 mg, 71% yield; R$_f$=0.27 (2:1 hexane EtOAc); $^1$H NMR (CDCl$_3$) δ 7.58 (dd, J=7.8 and 1.5 Hz, 1 H, Ar), 7.15 (dd, J=7.8 and 1.5 Hz, 1 H, Ar), 6.77 (t, J=7.8 Hz, 1 H, Ar), 6.09 (m, 1 H, HC=C), 6.01 (m, 1 H, HC=C), 5.11 (m, 1 H, CHOAr), 4.68 (m, 1 H, CHOH), 4.12 (q, J=7.2 Hz, 2 H, OCH$_2$), 2.85 (m, 2 H), 2.60 (ddd, J=15.3 and 9.6 and 6.0 Hz, 1 H, CH$_2$ in cyclopentane), 2.30 (dt, J=1.8 and 6.9 Hz, 2 H), 2.06 (dt, J=14.7 and 3.9 Hz, 1 H, CH$_2$ in cyclopentane), 1.88 (m, 2 H), 1.25 (t, J=6.3 Hz, 3 H, CH$_3$), 0.88 (m, 1 H, OH); $^{13}$C NMR (CDCl$_3$) δ 173.69, 156.22, 138.09, 137.98, 136.65, 133.55, 130.56, 125.87, 92.45, 85.71, 74.97, 60.52, 41.28, 33.50, 30.86, 25.47, 14.28; IR (neat) 3350 (OH, 2959, 1720 (C=O), 1599, 1462, 1352 cm$^{-1}$; HRMS m/z calculated for C$_{17}$H$_{21}$O$_4$I 416.04847, found 416.04747.

EXAMPLE 9

Preparation of Compound 16

In a vial were placed compound 9 (94 mg, 0.23 mmol), 1-octen-3-one (285 mg, 2.3 mmol), n-Bu$_4$NCl (Lancaster, 70 mg, 0.25 mmol), i-Pr$_2$NEt (98 μL, 0.58 mmol), Pd(OAc)$_2$ (2.5 mg, 0.011 mmol) and DMF (0.46 ml). After the reaction was stirred for 12 hr. at 50° C., it was poured into 40 ml of EtOAc. The mixture was washed with saturated NH$_4$Cl (15 ml) and then the aqueous phase was back-extracted with EtOAc (15 ml). The overall organic phase was washed with brine (15 ml), and then dried over MgSO$_4$ and concentrated under reduced pressure. The residue was purified by flash chromatography to give product 16: 37 mg, 42% yield; R$_f$=0.44 (1:1 hexane/EtOAc); $^1$H NMR (CDCl$_3$) δ 6.94 (d, J=7.5 Hz, 1 H, Ar), 6.88 (d, J=7.5 Hz, 1 H, Ar), 6.85 (dd, J=15.9 and 9.9 Hz, 1 H, C=CH), 6.75 (t, J=7.5 Hz, 1 H, Ar), 6.21 (d, J=19.5 Hz, 1 H, HC=C), 5.39 (dd, J=8.1 and 6.0 Hz, 1 H, CHOAr), 4.30 (m, 1 H, CHOH), 4.12 (m, 2 H), 3.99 (t, J=8.4 Hz, 1 H), 2.85 (dt, J=3.9 and 9.6 Hz, 1 H), 2.55 (m, 4 H), 2.26 (m, 2 H), 2.18 (ddd, J=15.3 and 6.0 and 4.5 Hz, 1 H, CH$_2$ in cyclopentane), 2.02 (m, 2 H), 1.88 (m, 1 H), 1.63 (m, 2 H), 1.28 (m, 7 H, CH$_2$'s and OCH$_2$CH$_3$), 0.89 (t, J=6.9 Hz, 3 H, CH$_3$); $^{13}$C NMR (CDCl$_3$) δ 200.94, 173.79, 157.68, 144.27, 132.17, 129.05, 127.05, 123.61, 123.20, 120.06, 88.92, 76.69, 60.26, 52.63, 50.69, 43.01, 38.94, 33.36, 31.46, 28.94, 24.81, 24.00, 22.42, 14.22, 13.90; IR (neat) 3464 (OH), 2932, 1732 (C=O), 1688 (C=O), 1465 cm$^{-1}$; HRMS m/z calculated for C$_{25}$H$_{34}$O$_5$ 414.24063, found 414.24118.

EXAMPLE 10

Preparation of Compounds 17 (R=Et) and 18 (R=Et)

To a solution of LiAlH$_4$ (Aldrich, 2.8 ml, 0.539 M in THF, 1.52 mmol) was added ethanol (0.76 ml, 2 M in THF, 1.52 mmol) dropwise over 10 min. at room temperature. Subsequently, a THF solution of (S)-binaphthol (Aldrich, 429 mg, 1.52 mmol in 2.4 ml of THF) was added dropwise, and the resulting mixture was stirred for 30 min. Enone 16 (199 mg, 0.51 mmol) in 2 ml of THF was added dropwise over 3 min. at −100° C., and stirring was continued for 2 hr at −100° C. and for another 2 hr at −78° C. The reaction was quenched by adding methanol (0.5 ml) at −78° C. and warmed to room temperature. After addition of water (0.5 ml) and ether (15 ml), stirring was continued for an additional 30 min. To this mixture was added anhydrous MgSO$_4$ and the mixture was filtered through Celite. Concentration, followed by flash chromatography with 1:2 hexane/EtOAc, gave compounds 17 (R=Et, 49 mg, 25% yield) and 18 (R=Et, 50 mg, 25% yield).

Compound 17 (R=Et): R$_f$=0.25 (1:2 hexane/−EtOAc); $^1$H NMR (CDCl$_3$) δ 6.91 (d, J=7.5 Hz, 2 H, Ar), 6.73 (t, J=7.5 Hz, 1 H, Ar), 5.66 (m, 2 H, HC=CH), 5.33 (t, J=7.8 Hz, 1 H, CHOAr), 4.20 (m, 1 H, CHOH), 4.10 (m, 3 H, OCH$_2$ and C=CHCHOH), 3.87 (t, J=8.7 Hz, CHAr), 2.74 (m, 1 H), 2.64 (dd, J=12.9 and 6.6 Hz, 1 H), 2.55 (dt, J=21.3 and 7.2 Hz, 1 H), 2.38 (d, J=15.0 Hz, 1 H, CH$_2$ in cyclopentane), 2.27 (dt, J=2.1 and 1.8 Hz, 1 H), 2.15 (ddd, J=15.0 and 6.0 and 4.5 Hz, 1 H, CH$_2$ in cyclopentane), 2.04–1.78 (m, 4 H), 1.67 (br s, 2 H, OH's), 1.54 (m, 1 H), 1.33 (m, 6 H), 1.25 (t, J=7.5 Hz, 3 H, CH$_3$), 0.92 (t, J=6.3 Hz, CH$_3$); $^{13}$C NMR (CDCl$_3$) δ 173.90, 157.81, 136.44, 128.73, 128.15, 127.76, 123.91, 122.99, 119.82, 88.28, 76.93, 72.96, 60.30, 52.28, 50.04, 42.37, 37.04, 33.52, 31.81, 29.06, 25.25, 24.89, 22.69, 14.29, 14.10; IR (neat) 3486 (OH), 1732 (C=O) cm$^{-1}$; HRMS m/z calculated for C$_{25}$H$_{36}$O$_5$ 416.25628, found 416.25541.

Compound 18 (R=Et): R$_f$=0.48 (1:2 hexane/−EtOAc); $^1$H NMR (CDCl$_3$) δ 6.97 (d, J=7.2 Hz, 1 H, Ar), 6.92 (d, J=7.5 Hz, 1 H, Ar), 6.74 (t, J=7.5 Hz, 1 H, Ar), 5.71 (m, 2 H, HC=CH), 5.34 (t, J=6.9 Hz, 1 H, CHOAr), 4.19 (m, 1 H, CHOH), 4.11 (m, 3 H, OCH$_2$ and C=CHCHOH), 3.90 (t, J=11.7 Hz, 1 H, CHAr), 2.75 (m, 1 H), 2.59 (m, 1 H), 2 38 (d, J=15.0 Hz, 1 H, CH$_2$ in cyclopentane), 2.27 (m, 2 H), 2.16 (ddd, J=15.0 and 6.0 and 4.5 Hz, 1 H, CH$_2$ in cyclopentane), 2.05–1.82 (m, 4 H), 1.72 (d, J=6.0 Hz, 1 H), 1.53 (br s, 2 H, OH's), 1.29 (m, 6 H), 1.25 (t, J=7.5 Hz, 3 H, CH$_3$), 0,88 (m, 3 H, CH$_3$); $^{13}$C NMR (CDCl$_3$) δ 173.87, 157.69, 136.34, 128.70, 127.76, 127.08, 124.04, 122.95, 119.85, 88.23. 77.02, 72.53, 60.27, 52.38, 50.06, 42.52, 37.27, 33.49, 31.80, 29.04, 25.19, 24.86, 22.63, 14.27, 14.10; IR (neat) 3416 (OH), 3053, 2845, 1732 (C=O), 1599, 1447 cm$^{-1}$; HRMS m/z calculated for $C_{25}H_{36}O_5$ 416.25628, found 416.25711.

EXAMPLE 11

Preparation of Compounds 17 (R=Et) and 19 (R=Et)

In a vial were placed compound 9 (109 mg, 0.26 mmol), γ-stannyl alcohol 14 (164 mg, 0.39 mmol), i-Pr$_2$NEt (85 mg, 0.66 mmol), n-Bu$_4$NCl (Lancaster, 88 mg, 0.31 mmol), Pd(OAc)$_2$ (2.9 mg, 0.013 mmol) and DMF (0.52 ml) as a solvent. After the resulting mixture was stirred for 12 hr. at room temperature, it was passed through a silica gel pad with 1:2 hexane/EtOAc. The solution was concentrated, and the residue was purified by flash chromatography with 1:2 hexane/EtOAc to give compounds 17 (R=Et, 15 mg, 14% yield) and 19 (R=Et, 17 mg, 16% yield). The spectral data for compound 19 are the same as those of compound 18 (R=Et).

EXAMPLE 12

Preparation of 12-epi-5,6,7-trinor-4,8-inter-m-phenylene PGI$_2$ [17 (R=H)].

To a solution of compound 17 (R=Et, 22 mg, 0.06 mmol) in 0.74 ml of THF was added 3 N aqueous NaOH (0.37 ml) at room temperature. After the mixture was stirred for 6 days at room temperature, it was neutralized by 2 N aqueous HCl. The organic phase was decanted with EtOAc, and then dried over MgSO$_4$. Concentration, followed by flash chromatography with 20:1 EtOAc/MeOH, gave product 17 (R=H): 17 mg, 83% yield; R$_f$=0.29 (20:1 EtOAc/MeOH); $^1$H NMR (CDCl$_3$) δ 6.90 (d, J=7.5 Hz, 1 H, Ar), 6.89 (d, J=7.5 Hz, 1 H, Ar), 6.72 (t, J=7.5 Hz, 1 H, Ar), 5.61 (m, 2 H, HC=CH), 5.31 (dd, J=0.9 and 7.8 Hz, 1 H, CHOAr), 4.30 (br s, 2 H, OH's), 4.18 (m, 1 H, CHOH), 4.03 (m, 1 H, C=CCHOH), 3.85 (t, J=9.0 Hz, 1 H, CHAr), 2.75-2.65 (m, 2 H), 2.53 (m, 1 H), 2.36 (d, J=15.0 Hz, 1 H, CH$_2$ in cyclopentane), 2.26 (m, 2 H), 2.17-2.01 (m, 2 H), 1.81 (m, 1 H), 1.53 (m, 3 H), 1.32 (m, 6 H), 0.91 (t, J=6.9 Hz, 3 H, CH$_3$) $^{13}$C NMR (CDCl$_3$) δ 177.93, 157.99, 136.35, 128.91, 128.29, 127.65, 123.97, 122.80, 119.98, 88.37, 77.00, 73.04, 52.18, 49.95, 42.02, 36.96, 32.89, 31.83, 28.83, 25.28, 24.85, 22.73, 14.12; IR (neat) 3383 (OH), 2928, 1709 (C=O), 1595, 1454 cm$^{-1}$; HRMS m/z calculated for $C_{23}H_{32}O_5$ 388.22497, found 388.22406. Anal. Calcd for $C_{23}H_{32}O_5$: C, 71.11; H, 8.30. Found: 70.75; H, 8.92.

EXAMPLE 13

Preparation of 12,15-epi-5,6,7-trinor-4,8-inter-m-phenylene PGI$_2$ [18 (R=H)].

To a solution of compound 18 (R=Et, 55 mg, 0.14 mmol) in 1.8 ml of THF was added 3 N aqueous NaOH (0.9 ml) at room temperature. After the reaction was stirred for 6 days at room temperature, it was neutralized by 2 N aqueous HCl. The organic phase was decanted with ethyl acetate and dried over MgSO$_4$. Concentration in vacuo followed by flash chromatography with 20:1 EtOAc/MeOH gave compound 18 (R=H): 47 mg, 92% yield; R$_f$=0.37 (20:1 EtOAc/MeOH); $^1$H NMR (CDCl$_2$) δ 6.94 (d, J=7.5 Hz, 1 H, Ar), 6.90 (d, J=7.5 Hz, 1 H, Ar), 6.74 (t, J=7.5 Hz, 1 H, Ar), 5.72 (dd, J=15.3 and 5.1 Hz, 1 H, HC=C), 5.65 (dd, J=15.3 and 7.8 Hz, 1 H, C=CH), 5.62 (br s, 2 H, OH's), 5.32 (t, J=6.9 Hz, 1 H, CHOAr), 4.20 (m, 1 H, CHOH), 4.12 (dd, J=12.0 and 9.0 Hz, 1 H, C=CHCHOH), 3.89 (t, J=8.7 Hz, 1 H), 2.80 (dt, J=4.2 and 9.0 Hz, 1 H), 2.70 (m, 1 H), 2.54 (m, 1 H), 2.38 (d, J=15.9 Hz, 1 H, CH$_2$ in cyclopentane), 2.29 (dd, J=14.1 and 6.3 Hz, 2 H), 2.22-2.04 (m, 2 H), 1.84 (m, 1 H), 1.49 (m, 3 H), 1.29 (m, 6 H), 0.89 (t, J=6.3 Hz, 3 H, CH$_3$); $^{13}$C NMR (CDCl$_3$) δ 178.54, 157.87, 136.26, 128.88, 127.64, 126.73, 124.15, 122.72, 119.92, 88.00, 76.93, 72.39, 52.27, 49.92, 42.12, 37.19 33.07, 31.81, 28.97, 25.17, 24.64, 22.64, 14.13; IR (neat) 3412 (OH), 3271 (OH), 3063, 2924, 2858, 1709 (C=O), 1456, 1254 cm$^{-1}$; HRMS m/z calculated for $C_{23}H_{32}O_5$ 388.22497, found 388.22589. Anal. Calcd for $C_{23}H_{32}O_5$; C, 71.11; H, 8.30. Found: C, 70.36, H, 8.09.

All patents, patent documents and publications cited herein are incorporated by reference herein, as though fully set forth.

The invention has been described with reference to various specific and preferred embodiments and techniques. However, it should be understood that many variations and modifications may be made while remaining within the spirit and scope of the invention.

What is claimed is:

1. A method for preparing benzoprostacyclins comprising reacting a compound of the general formula (III):

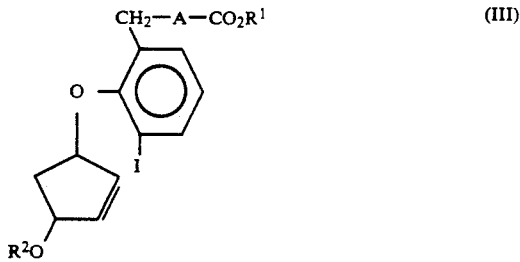

wherein R$^1$ is a pharmaceutically-acceptable cation, H or (C$_1$–C$_{12}$)alkyl; A is —CH$_2$—, —O—CH$_2$—, CH$_2$—CH$_2$— or —CH=CH—; and R$^2$ is H, (C$_1$–C$_{12}$)alkyl, (C$_2$–C$_{10}$)acyl or (C$_7$–C$_{13}$)aroyl with a molar excess compound of a general formula (IV):

wherein R$^5$ is (C$_1$–C$_5$)alkyl; B is —(CH$_2$)$_n$—Z wherein n is 0–4 and Z is —CH$_2$CH$_2$—, —CH=CH— or —C≡C—; R$^4$ is H, F, CH$_3$ or CH$_2$CH$_3$; and R$^7$ is ((C$_1$–C$_4$)alkyl)$_3$Sn, (phenyl)$_3$Sn or H; R$^8$ is H or (C$_1$–C$_{12}$)alkyl; and R$^9$ is OR$^3$, wherein R$^3$ is H, (C$_1$–C$_{12}$)alkyl, (C$_2$–C$_{10}$)acyl or (C$_7$–C$_{13}$)aroyl, or R$^8$ and R$^9$ taken together are keto; wherein the reaction is carried out at about 20°-75° C. for about 5–48 hrs in an organic solvent in the presence of a catalytic amount of Pd(O), and an organic amine to yield a compound of the formula (II):

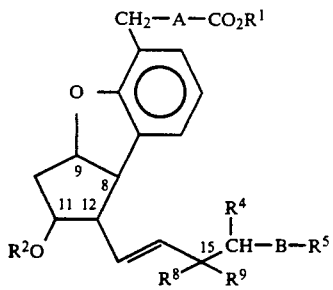

(II)

wherein $R^1$, A, $R^2$, $R^8$, $R^9$, $R^4$, B and $R^5$ are as defined above.

2. The method of claim 1, wherein $R^8$ and $R^9$ taken together are keto in compound II, further comprising reducing the $C_{15}$-keto group of compound II with a reducing agent to yield a compound of formula II wherein $R^8$ is H and $R^9$ is OH.

3. The method of claim 1 wherein $R^7$ is (n-butyl)$_3$Sn, $R^8$ is H and $R^9$ is OH.

4. The method of claim 1, wherein compound II comprises (S)$C_{15}$—OH.

5. The method of claim 4 wherein the $C_{11}$—$OR^2$ bond is in the alpha-configuration.

6. The method of claim 1 wherein, in compound III, $R^1$ is ($C_1$-$C_{12}$)alkyl and $R^2$ is H.

7. The method of claim 6, further comprising saponifying the $CO_2R^1$ moiety of compound II to yield $CO_2H$.

8. The method of claim 7, further comprising forming a pharmaceutically-acceptable alkali metal salt, ammonium, or amine salt of the moiety $CO_2H$.

9. The method of claim 1 wherein the Pd(O) is formed in situ from a Pd(II) compound.

10. The method of claim 9 wherein the Pd(II) compound is Pd(OAc)$_2$.

11. The method of claim 1 wherein the organic base comprises a tri($C_2$-$C_{12}$)alkylamine.

12. The method of claim 11 wherein the organic amine comprises diisopropyl(ethyl)amine.

13. The method of claim 1 wherein the mole ratio of III:IV is about 1:1.25-20.

14. The method of claim 6 wherein A is —CH$_2$— or —CH$_2$—CH$_2$— and B is CH$_2$—CH$_2$—CH$_2$.

15. The method of claim 14 wherein $R^4$ is H and $R^5$ is CH$_3$.

* * * * *

UNITED STATES PATENT AND TRADEMARK OFFICE
CERTIFICATE OF CORRECTION

PATENT NO. : 5,233,059
DATED : August 3, 1993
INVENTOR(S) : Richard C. Larock, et al It is certified that error appears in the above-indentified patent and that said Letters Patent is hereby corrected as shown below:

At Column 1, line 30, please delete

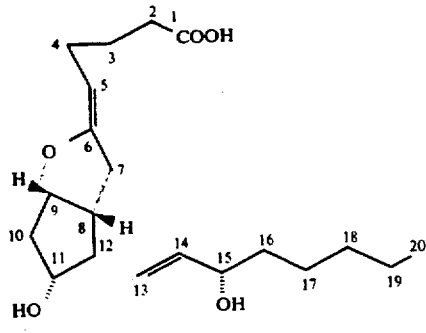

I

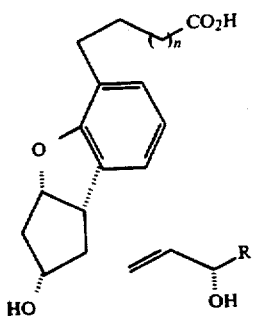

|    | n | R |
|----|---|---|
| Ia | 1 | $n$-$C_5H_{11}$ |
| Ib | 1 | $CH(Me)CH_2C\equiv CCH_3$ |
| Ic | 0 | $n$-$C_5H_{11}$ | and insert

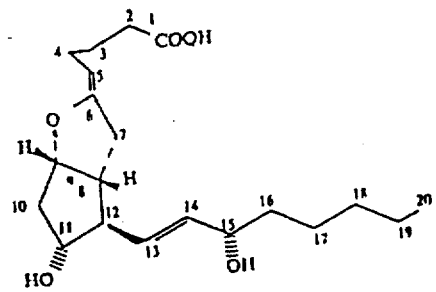

I

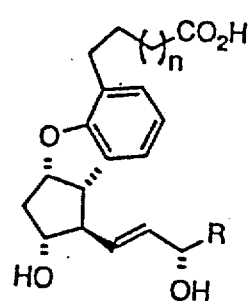

|    | n | R |
|----|---|---|
| Ia | 1 | $n$-$C_5H_{11}$ |
| Ib | 1 | $CH(Me)CH_2C\equiv CCH_3$ |
| Ic | 0 | $n$-$C_5H_{11}$ |

UNITED STATES PATENT AND TRADEMARK OFFICE
CERTIFICATE OF CORRECTION

PATENT NO. : 5,233,059
DATED : August 3, 1993
INVENTOR(S) : Richard C. Larock, et al It is certified that error appears in the above-indentified patent and that said Letters Patent is hereby corrected as shown below:

At Column 2, lines 58-63, please delete

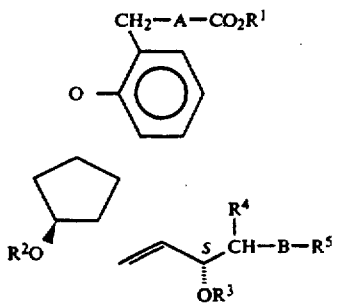

(IIb)

and insert

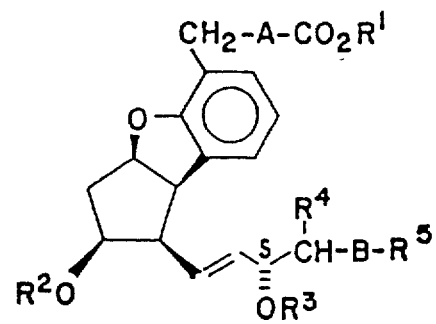

(IIb)

UNITED STATES PATENT AND TRADEMARK OFFICE
CERTIFICATE OF CORRECTION

PATENT NO. : 5,233,059
DATED : August 3, 1993
INVENTOR(S) : Richard C. Larock, et al It is certified that error appears in the above-indentified patent and that said Letters Patent is hereby corrected as shown below:

At Column 4, lines 32-39, please delete           and insert

| | | | $R^1$ | $R^2$ |
|---|---|---|---|---|
| 1 (R = H) | a | 3 | H | $CH_2CH=CH_2$ |
| 2 (R = allyl) | c | 4 | TBDMS | $CH_2CH=CH_2$ |
| | d | 5 | TBDMS | $CH_2CHO$ |
| | e | 6 | TBDMS | $E-CH_2CH=CHCO_2Et$ |
| | f | 7 | TBDMS | $(CH_2)_3CO_2Et$ |
| | g | 8 | H | $(CH_2)_3CO_2Et$ |

| | | | $R^1$ | $R^2$ |
|---|---|---|---|---|
| 1 (R = H) | a | 3 | H | $CH_2CH=CH_2$ |
| 2 (R = allyl) | c | 4 | TBDMS | $CH_2CH=CH_2$ |
| | d | 5 | TBDMS | $CH_2CHO$ |
| | e | 6 | TBDMS | $E-CH_2CH=CHCO_2Et$ |
| | f | 7 | TBDMS | $(CH_2)_3CO_2Et$ |
| | g | 8 | H | $(CH_2)_3CO_2Et$ |

At Column 4, line 66, please delete "43%" and insert --42%--.

At Column 6, lines 61-62, please delete "(p-tolylsionitrile)" and insert --(p-tolylisonitrile)--.

At Column 7, lines 64-65, please delete "carboyxlic" and insert --carboxylic--.

At Column 9, line 44, please delete both "CH" and insert twice --HC--.

UNITED STATES PATENT AND TRADEMARK OFFICE
CERTIFICATE OF CORRECTION

PATENT NO. : 5,233,059
DATED : August 3, 1993
INVENTOR(S) : Richard C. Larock, et al It is certified that error appears in the above-indentified patent and that said Letters Patent is hereby corrected as shown below:

At Column 10, line 40, please delete "CH" and insert --HC--.

At Column 10, line 68, please delete "$CH_2$)," and insert --$CH_3$),--.

At Column 12, line 5, please delete "CHOH)," and insert --C$\underline{H}$OH),--.

At Column 12, line 9, please delete "$CH_3$)," and insert --C$\underline{H}_3$),--

At Column 12, line 43, please delete "CHOH)," and insert --C$\underline{H}$OH),--.

At Column 12, line 43, please delete "CHCHOH)," and insert --CHC$\underline{H}$OH),--.

At Column 12, line 61, please delete "CHOH)," and insert --C$\underline{H}$OH),--.

At Column 12, line 62, please delete "CHCHOH)," and insert --CHC$\underline{H}$OH),--.

UNITED STATES PATENT AND TRADEMARK OFFICE
CERTIFICATE OF CORRECTION

PATENT NO. : 5,233,059
DATED : August 3, 1993
INVENTOR(S) : Richard C. Larock, et al It is certified that error appears in the above-indentified patent and that said Letters Patent is hereby corrected as shown below:

At Column 13, line 40, please delete "CHOH)," and insert --C$\underline{H}$OH),--.

At Column 13, line 41, please delete "CCHOH)," and insert --CC$\underline{H}$OH),--.

At Column 14, line 3, please delete "CHOH)," and insert --C$\underline{H}$OH),--.

At Column 14, line 5, please delete "CHCHOH)," and insert --CHC$\underline{H}$OH),--.

Signed and Sealed this

Sixteenth Day of September, 1997

Attest:

BRUCE LEHMAN

*Attesting Officer*    *Commissioner of Patents and Trademarks*